(12) United States Patent
Han

(10) Patent No.: US 9,610,147 B2
(45) Date of Patent: *Apr. 4, 2017

(54) BRUSH HEAD

(71) Applicant: Mei-Ling Pauling Han, Rowland Heights, CA (US)

(72) Inventor: Mei-Ling Pauling Han, Rowland Heights, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/151,774

(22) Filed: Jan. 9, 2014

(65) Prior Publication Data

US 2014/0123418 A1 May 8, 2014

Related U.S. Application Data

(63) Continuation of application No. 12/932,533, filed on Feb. 25, 2011, now Pat. No. 8,657,518.

(51) Int. Cl.
| | |
|---|---|
| *A46B 11/06* | (2006.01) |
| *A61C 15/00* | (2006.01) |
| *A46B 5/00* | (2006.01) |
| *A46B 11/00* | (2006.01) |
| *A61C 17/02* | (2006.01) |

(52) U.S. Cl.
CPC ............ *A61C 15/00* (2013.01); *A46B 5/0095* (2013.01); *A46B 11/001* (2013.01); *A46B 11/002* (2013.01); *A46B 11/063* (2013.01); *A61C 17/02* (2013.01); *A46B 2200/108* (2013.01)

(58) Field of Classification Search
CPC ............ A46B 2200/108; A46B 11/063; A46B 11/001
USPC ................ 401/289; 433/80, 82, 89
See application file for complete search history.

(56) References Cited

U.S. PATENT DOCUMENTS

| | | | | |
|---|---|---|---|---|
| 3,636,947 A * | 1/1972 | Balamuth | ............... | A61C 17/20 15/22.1 |
| 4,780,923 A * | 11/1988 | Schultheiss | ............... | A46B 7/04 15/111 |
| 4,875,602 A * | 10/1989 | Chickering | ........... | A45D 34/042 222/187 |
| 6,932,603 B2 * | 8/2005 | Han | ......................... | A46B 3/18 401/290 |
| 6,932,604 B2 * | 8/2005 | Han | ......................... | A46B 3/18 401/290 |
| 7,232,310 B2 * | 6/2007 | Han | ......................... | A46B 7/04 401/290 |
| 7,699,608 B2 * | 4/2010 | Han | ......................... | A46B 3/18 433/80 |

\* cited by examiner

*Primary Examiner* — Jennifer C Chiang
(74) *Attorney, Agent, or Firm* — Raymond Y. Chan; David and Raymond Patent Firm

(57) ABSTRACT

An interproximal squirt brush, includes a solution container having a solution chamber for containing a solution and a hollow nozzle head having an opening communicating with the solution chamber; and a brush head having an elongated retention portion replaceably coupling at the opening of the nozzle head and a brush portion extended from the retention portion, wherein a clearance is formed between the opening and the retention portion of the brush head for enabling the solution from the solution chamber being discharged to the brush portion of the brush head along the retention portion.

11 Claims, 4 Drawing Sheets

BRUSH HEAD

CROSS REFERENCE OF RELATED APPLICATION

This is a Continuation application that claims the benefit of priority under 35 U.S.C. §119 to a non-provisional application, application Ser. No. 12/932,533, filed Feb. 25, 2011.

BACKGROUND OF THE PRESENT INVENTION

Field of Invention

The present invention relates to a squirt brush, and more particular to an interproximal squirt brush, wherein a brush head is replaceably coupled with a solution container for dispensing solution from the solution container to the brush head, wherein the solution container has a stopper which stops/controls the solution to be drawn back into the solution container.

Description of Related Arts

A squirt brush is commonly used in medical field or in cosmetic industry. For example, the squirt brush in medical/dental field can be used to clean inner layer and outer layer of the enamel of the teeth as a tooth cleaning tool. Generally speaking, the squirt brush comprises a solution container and a brush head affixed thereto such that the solution inside the solution container can be discharged to the brush head, such as wad of cotton or an applicator tip made of different kinds of materials.

Accordingly, gum disease (periodontitis) is one of the common dental problems. Periodontal disease, especially in the early stages, is usually not painful such that many people having gum disease do not even realize it. Researches report that the periodontal disease is an infection in the gums caused by the bacteria in plaque, wherein plaque and bacteria build up on and between the teeth. In addition, according to the research done by China Times 2009, gum disease (periodontitis) can cause coronary heart disease, stroke, and diabetes. To prevent the gum disease, dentists always suggest having a better oral hygiene by brushing and flossing regularly via the traditional interproximal brush. In addition, mouthwash is also considered as one of the effective methods for removing plaque and bacteria. By reducing the amount of plaque on your teeth, you can reduce the amount of bacteria in your mouth.

Brushing method is the most common method for removing plaque built-up on the teeth. However, due to the structure of the toothbrush, the bristles of the toothbrush cannot effectively remove the plaque from the areas between teeth and around the gums. Therefore, flossing becomes the effective way to help the user to remove plaque and debris from between the teeth, especially the areas inaccessible to the toothbrush. It is ideal to use the mouthwash after brushing and/or flossing since the mouthwash with medicament is capable of not only effectively removing oral bacteria and stain on the teeth but also reducing bad breath.

However, the flossing technique of holding the floss by hand leads to different operational result depending on the users. Flossing requires the user to floss up, down, right, left, front, and back. This six-step process is too cumbersome and time consuming. Therefore, the conventional floss is disadvantageous in practical use. An improved toothpick, which combines the advantages of both toothbrush, floss, and mouthwash, comprises a brush head having a size adapted to fit between the teeth and gum line to brush the areas thereof. Due to the friction between the brush head and the gum line, tenderness during dry brushing always gives discomfort to the user. An improper brushing the gum line may even cause the gum bleeding.

Therefore, the squirt brush can achieve the above mentioned advantages by discharging the mouthwash solution in the container body to the brush head while the brush head is small enough to fit between the teeth for removing the plaque from the areas between teeth and around the gums.

Another example of the squirt brush being commonly used in cosmetic industry forms a cotton swab apparatus. Instead of having a tooth brushing type brush head for medical use, the squirt brush for cosmetic industry comprises a small wad of cotton wrapped around one end of a brush arm such that the solution, such as cleaning solution or disinfecting solution, can be discharged from the solution container to the cotton end of the brush arm.

However, the squirt brush has a major drawback that the brush head cannot be replaced. In other words, once the brush head is affixed to the solution container, the squirt brush with both the brush head and the solution container must be disposed after use. Therefore, the squirt brush is considered as a one-time use apparatus or a disposable tool.

SUMMARY OF THE PRESENT INVENTION

The invention is advantageous in that it provides an interproximal squirt brush, wherein a brush head is replaceably coupled with a solution container for dispensing solution from the solution container to the brush head.

Another advantage of the invention is to an interproximal squirt brush, wherein a clearance is formed when the brush arm is replaceably coupled at an opening of the solution container for enabling the solution passing through the clearance towards the brush member.

Another advantage of the invention is to an interproximal squirt brush, wherein not only the brush head is replaceably mounted to the bottle container but also the washing solution can be refilled into the bottle container so as to extend the service life span of the interproximal squirt brush of the present invention. For example, the washing solution can be easily replaced by removing a rubber stopper at the bottom of the bottle container.

Another advantage of the invention is to an interproximal squirt brush, wherein the coupling operation of the brush head is simple and easy by one clip operation.

Another advantage of the invention is to an interproximal squirt brush, wherein only the brush head is replaced from the solution container so as to minimize the waste of the material of the present invention.

Another advantage of the invention is to an interproximal squirt brush, wherein no expensive or complicated structure is required to employ in the present invention in order to achieve the above mentioned objects. Therefore, the present invention successfully provides an economic and efficient solution not only for enabling the brush head to be replaced from the solution container but also enabling different types of brush heads to be used for the solution container.

Additional advantages and features of the invention will become apparent from the description which follows, and may be realized by means of the instrumentalities and combinations particular point out in the appended claims.

According to the present invention, the foregoing and other objects and advantages are attained by providing an interproximal squirt brush, which comprises a solution container and a brush head replaceably coupling with the solution container.

The solution container has a solution chamber for containing a solution and a hollow nozzle head having an opening communicating with the solution chamber.

The brush head has an elongated retention portion replaceably coupling at the opening of the nozzle head and a brush portion extended from the retention portion, wherein a clearance is formed between the opening and the retention portion of the brush head for enabling the solution from the solution chamber being discharged to the brush portion of the brush head along the retention portion.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
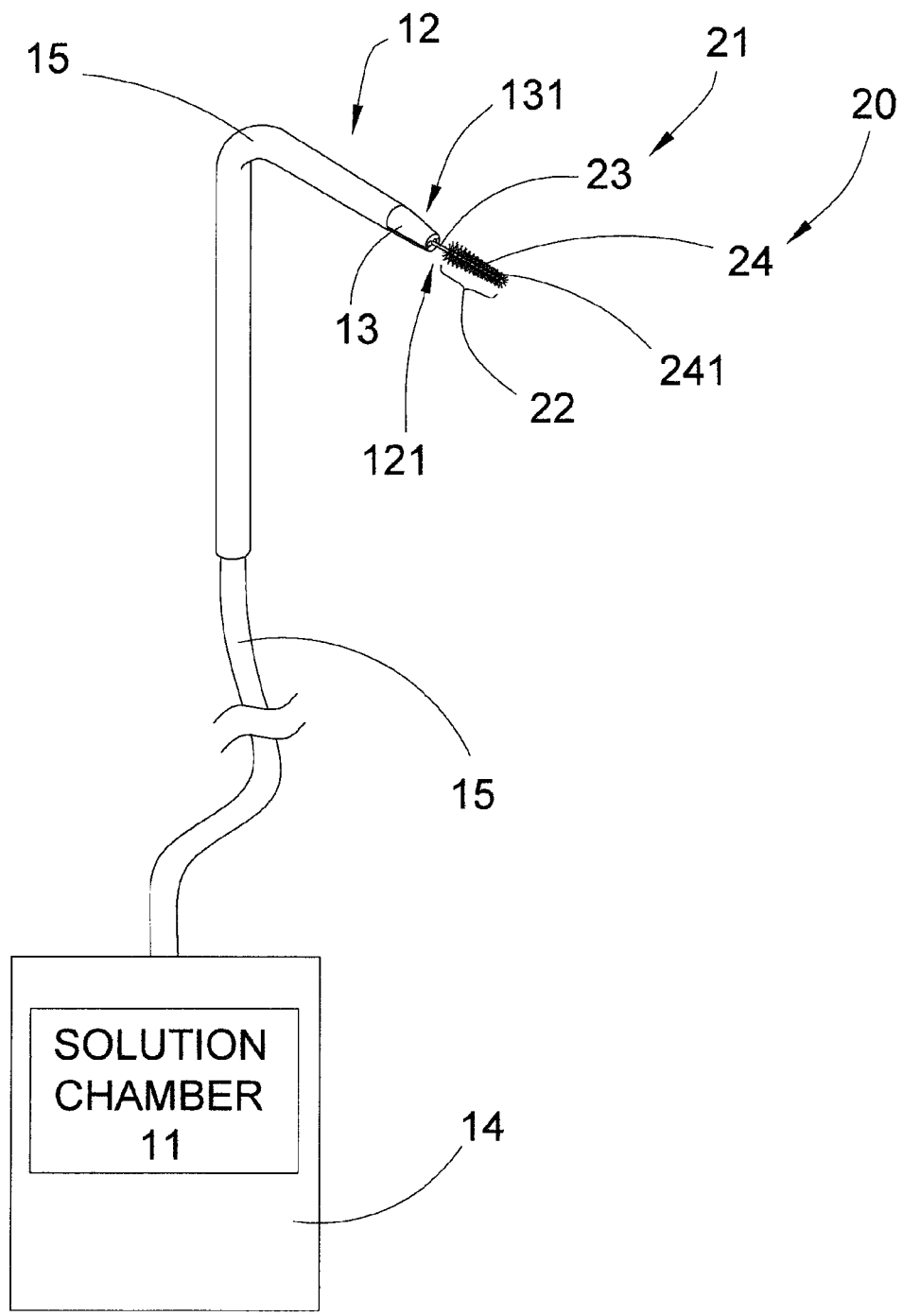
FIG. 1 is a perspective view of an interproximal squirt brush according to a preferred embodiment of the present invention.

Referring to FIG. 1 of the drawings, an interproximal squirt brush according to a preferred embodiment of the present invention is illustrated, wherein the interproximal squirt brush comprises a solution container 10 and a brush head 20.

The solution container 10 has a solution chamber 11 for containing a solution and a hollow nozzle head 12 having an opening 121 communicating with the solution chamber 11.

The brush head 20 has an elongated retention portion 21 replaceably coupling at the opening 121 of the nozzle head 12 and a brush portion 22 extended from the retention portion 21, wherein a clearance 201 is formed between the opening 121 and the retention portion 21 of the brush head 20 for enabling the solution from the solution chamber 11 being discharged to the brush portion 22 of the brush head 20 along the retention portion 21 thereof.

The solution container 10 comprises a solution supplier 14 defining the solution chamber 11 therein and an elongated solution delivering tube 15 extended from the solution supplier 14 to the nozzle head 12, wherein when the solution supplier 14 is actuated, such as operated by a pump device to controllably pump the solution to the nozzle head 12 through the solution delivering tube 15, the solution is discharged to the brush head 20 through the clearance 201.

Figure 2:
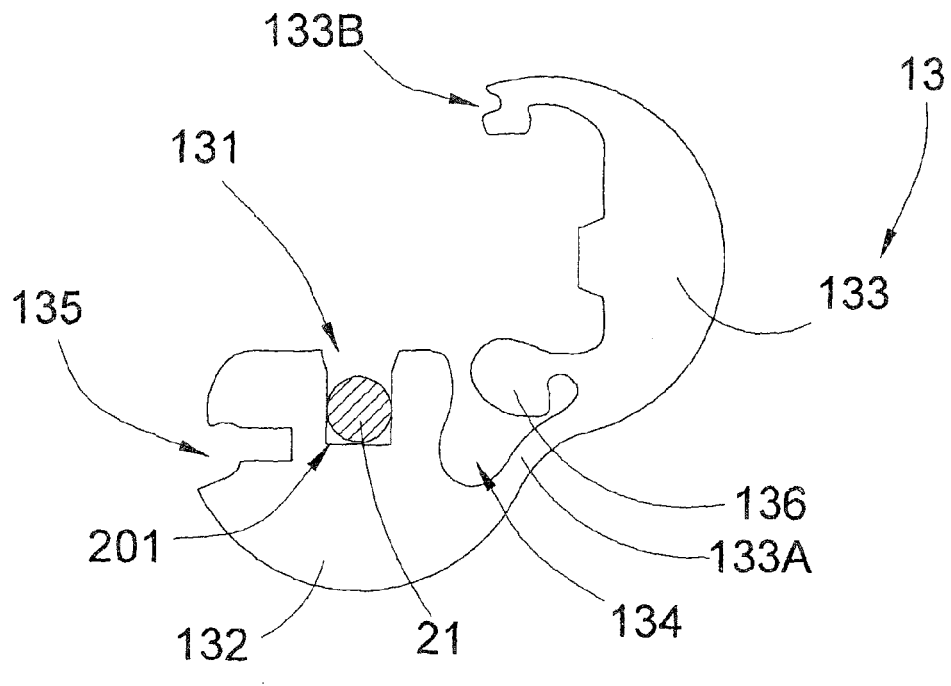
FIG. 2 is a sectional view of an elastic latch of the interproximal squirt brush according to the above preferred embodiment of the present invention, illustrating the elastic latch at an unlocked position.
Figure 3:
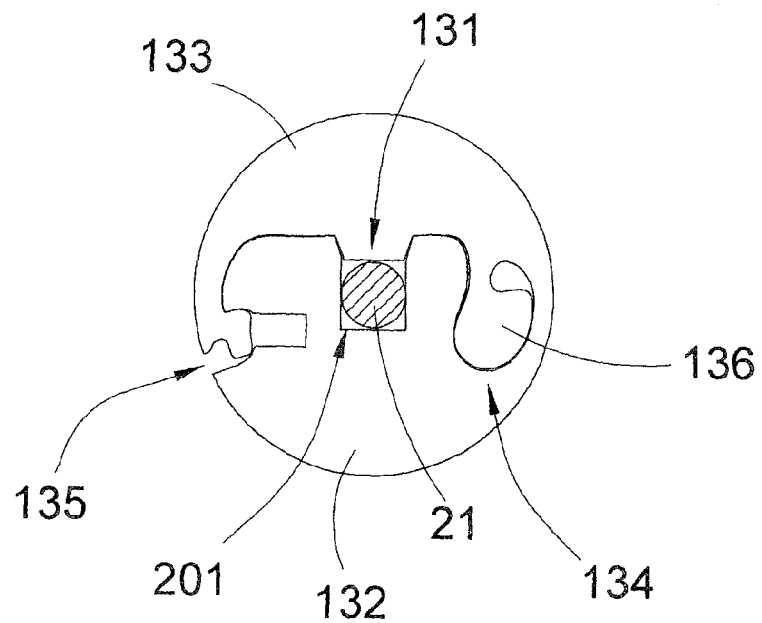
FIG. 3 is a sectional view of the elastic latch of the interproximal squirt brush according to the above preferred embodiment of the present invention, illustrating the elastic latch at a locked position.

As shown in FIGS. 2 and 3, the solution container 10 comprises an elastic latch 13 provided at the nozzle head 12 for detachably locking the retention portion 21 of the brush head 20 in position. Accordingly, the elastic latch 13, which is made of elastic material, is integrally formed with the nozzle head 12 at the opening 121 thereof to form a locking unit in order to detachably retain the brush head 20 in position.

The elastic latch 13 has a resilient channel 131 aligning with the opening 121 and arranged in such a manner that when the retention portion 21 of the brush head 20 is disposed along the resilient channel 131, the inner wall of the resilient channel 131 is slightly deformed to define the clearance 201 therebetween. In particular, the resilient channel 131 is formed at the opening 121 of the nozzle head 12, such that when the retention portion 21 of the brush head 20 is disposed along the resilient channel 131, the brush head 20 is held at the opening 121 of the nozzle head 12.

As shown in FIGS. 2 and 3, the elastic latch 13 comprises a holding member 132 defining the resilient channel 131 therealong, and a locking member 133 having one flexible edge 133A integrally extending from the holding member 132 and an opposed locking edge 133B detachably coupling with the holding member 132 to retain the retention portion 21 of the brush head 20 along the resilient channel 131.

As it is mentioned above, the elastic latch 13 is integrally formed with the nozzle head 12, wherein the holding member 132 forms at a bottom surrounding wall of the nozzle head 12 while the locking member 133 forms at a top surrounding wall of the nozzle head 12. Therefore, the brush head 20 can be directly coupled at the nozzle head 12 through the elastic latch 13.

The resilient channel 131 is longitudinally formed at the holding member 132 to align with the opening 121 of the nozzle head 12, wherein the resilient channel 131 has a rear opening communicating with the solution chamber 11 through the nozzle head 12, a front opening defining at the opening 121 of the nozzle head 12, and a top opening communicating between the front and rear openings. In other words, when the holding member 132 is folded on top of the locking member 133, the top opening of the resilient channel 131 is covered by the locking member 133 to form the elongated resilient channel 131 with front and rear openings.

In addition, the resilient channel 131 has a non-circular cross section and the retention portion 21 of the brush head 20 has a circular cross section, such that the clearance 201 is formed when the retention portion 21 of the brush head 20 is disposed along the resilient channel 131. Preferably, the resilient channel 131 has a rectangular cross section and defines two inner sidewalls to tangently contact with the retention portion 21 of the brush head 20.

As shown in FIG. 2, the flexible edge of the locking member 133 is integrally extended from the holding member 132 to form a one-piece integrated structure with a C-shaped clipping configuration. The locking member 133 is configured as a locking flap foldably extended form the holding member 132. Therefore, when the locking member 133 is folded to open up the top opening of the resilient channel 131, the retention portion 21 of the brush head 20 is adapted to slidably dispose in the resilient channel 131.

According to the preferred embodiment, the holding member 132 has a resilient cavity 134 provided close to the flexible edge of the locking member 132 and a latch cavity 135 provided at a sidewall of the holding member 132 and arranged in such a manner that when the locking member 133 is folded on the holding member 132 to engage the locking edge with the latch cavity 135, the resilient cavity 134 is slightly deformed to apply an resilient force at the locking edge of the locking member 133 so as to substantially lock up the locking member 133 with the holding member 132.

Accordingly, the resilient cavity 134 is longitudinally formed at the holding member 132 at a position adjacent to the resilient channel 131, wherein the resilient cavity 134 provides enough space for the locking member 132 to fold on the holding member 132. In addition, the locking member 133 further comprises a reinforcing member 136 integrally extended to fit into the resilient cavity 134 for ensuring the resilient force being transmitted to the locking edge of the locking member 133.

The reinforcing member 136 is integrally and downwardly extended from the bottom side of the locking member 133 to fit into the resilient cavity 134 when the locking member 133 is folded on top of the holding member 132. In particularly, the reinforcing member 136 has a tapered shape to ensure the reinforcing member 136 being fitting into the resilient cavity 134.

The latch cavity 135 is embodied as an elongated latch slot longitudinally formed at the sidewall of the holding member 132. The locking edge of the locking member 133 has a L-shaped hooking cross section to engage with the latch cavity 135 so as to latch up the locking member 133 with the holding member 132. Accordingly, the resilient channel 131 is positioned between the resilient cavity 134 and the latch cavity 135, wherein when the locking member 133 is folded to the holding member 132 that the reinforcing member 136 fits into the resilient cavity 134 and the locking edge of the locking member 133 engages with the latch cavity 135, the two sidewalls of the resilient channel 131 are pressed towards each other to slightly deform the size of the resilient channel 131. Therefore, the retention portion 21 of the brush head 20 is pressed between the two inner sidewalls of the resilient channel 131 to retain the brush head 20 in position. It is worth mentioning that the clearance 201 is formed between the two inner sidewalls of the resilient channel 131 for enabling the solution being discharged towards the brush portion 22 of the brush head 20. In addition, the resilient channel 131 provides enough resilient force at the inner sidewalls to retain the brush head 20 in position.

As shown in FIG. 1, the brush head 20 comprises an elongated brush arm 23 defining the retention portion 21 thereat, and a brush member 24 provided at a free end of the brush arm 23 to define the brush portion 22 thereat.

The brush arm 23, which is made of bendable material such as metal wire, is a twist wire arm, wherein the tail portion of the brush arm 23, i.e. the retention portion 21, is engaged within the resilient channel 131.

The brush member 24, according to the preferred embodiment, comprises a plurality of wire bristles 241, preferably made of nylon, radially extended from the brush arm 23 such that when the solution is discharged from the opening 121 of the nozzle head 12, the solution will be guided to flow along the brush arm 23 towards the wire bristles 241 of the brush member 24. In addition, the solution will then be guided to radially and outwardly flow at the wire bristles 241 such that solution will be retained at the wire bristles 241.

Accordingly, the brush head 20 of the preferred embodiment can used in medical field that the wire bristles 241 is adapted for fitting between the teeth and around the gum line to perform the brushing and/or flossing action so as to remove the stain and plaque on the teeth. In addition, when the solution in the solution container 10 is discharged, the solution is delivered to the wire bristles 241 of the brush member 24 through the opening 121 of the nozzle head 12.

Therefore, when the brush member 24 fits between the teeth and gum line during brushing process, the solution not only penetrates through the area between the teeth and around the gum line to remove the stain and bad breath, but also functions as a lubricant to minimize the friction between the brush member 24 and the gum line so as to control gum disease and reduce uncomfortable feeling to the user.

Figure 4:
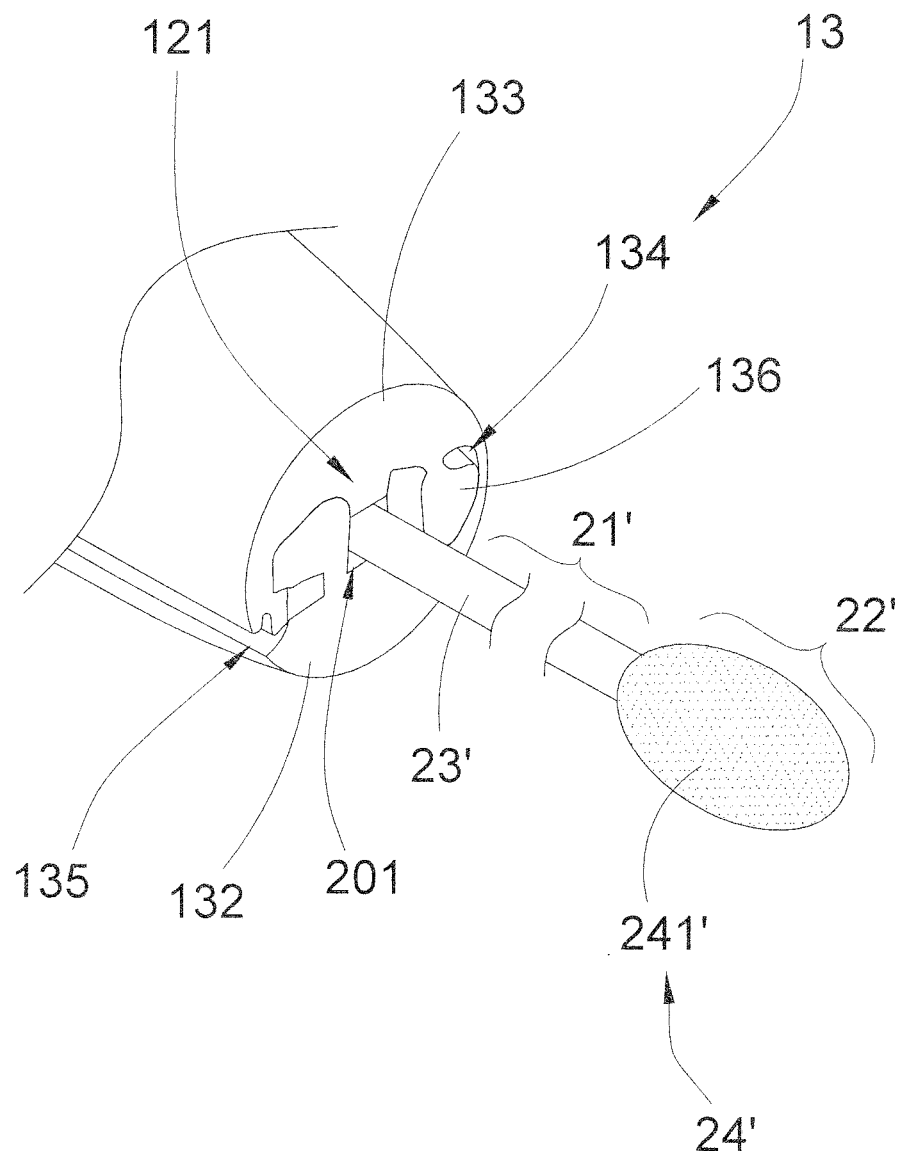
FIG. 4 illustrates an alternative mode of the solution container of the interproximal squirt brush according to the above preferred embodiment of the present invention.
Figure 5:
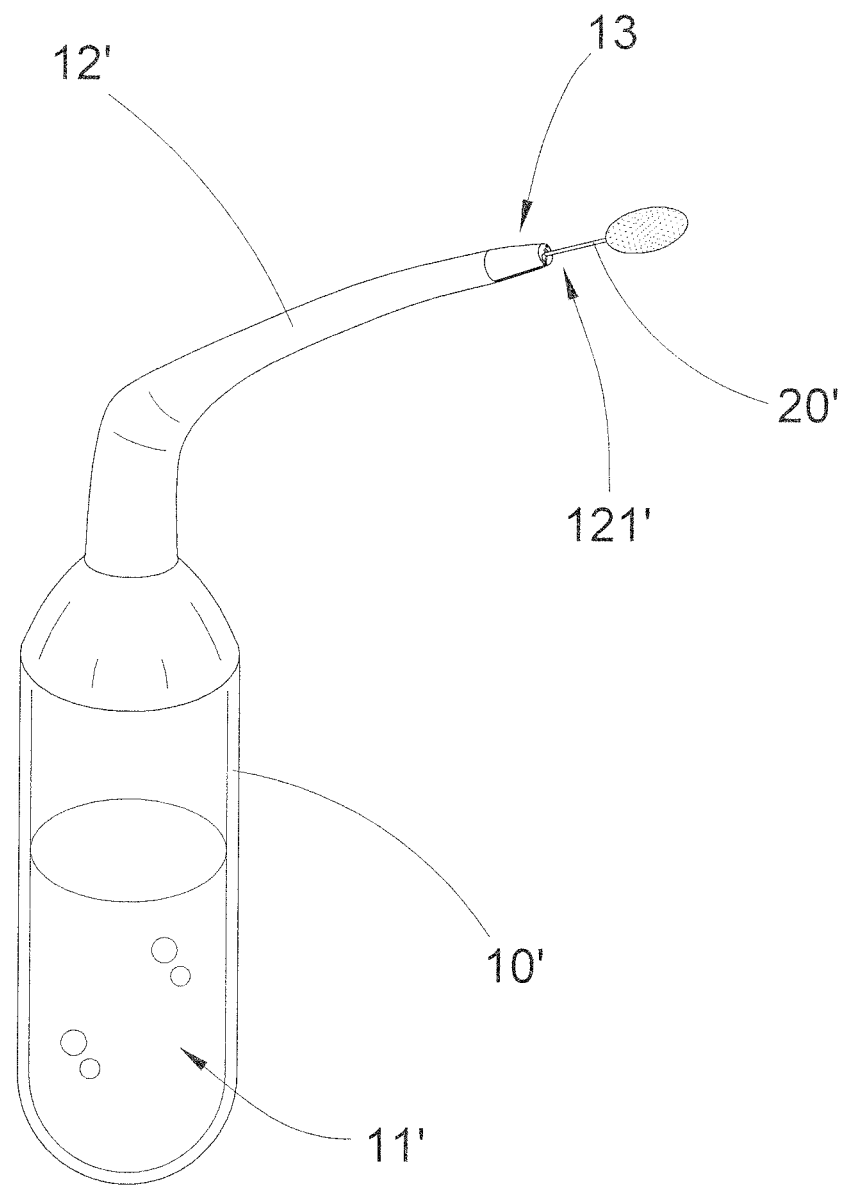
FIG. 5 illustrates an alternative mode of the brush head of the interproximal squirt brush according to the above preferred embodiment of the present invention.

FIGS. 4 and 5 illustrate an alternative mode of the brush head 20', wherein the brush head 20' comprises an elongated brush arm 23' defining the retention portion 21' thereat, and a brush member 24' provided at a free end of the brush arm 23' to define the brush portion 22' thereat.

The brush arm 23', which is made of bendable material such as metal wire, is a twist wire arm, wherein the tail portion of the brush arm 23', i.e. the retention portion 21', is disposed within the resilient channel 131'.

The brush member 24', according to the preferred embodiment, comprises a swab element 241' provided at the free end of the brush arm 23'. Preferably, the swab element 241' is a wad of cotton 241' wrapped around the free end of the brush arm 23' such that when the solution, such as cosmetic solution, is discharged from the opening 121' of the nozzle head 12', the solution will be guided to flow along the brush arm 23' towards the brush member 24'. In addition, the solution will then be guided to radially and outwardly flow at the swab element 241' such that the swab element 241' will absorb the solution from the inner portion to the outer portion so as to retain the solution at the swab element 241'.

It is appreciated that the brush member 23' comprises a scrub element provided at the free end of the brush arm 23', wherein the scrub element is a fibrous material such as nylon, polyurethane foam or polyolefins. In other words, the solution is delivered to the scrub element of the brush member 23' for providing the scrubbing process.

FIGS. 4 and 5 also illustrate an alternative mode of the solution container 10', wherein the solution container 10' is made of squeezable material arranged in such a manner that when the solution container 10' is squeezed, the solution therein is discharged at the opening 121' along the retention portion 21' of the brush head 20' to the brush portion 22' thereof through the clearance 201'. In particular, the cross section of the opening 121' of the solution container 10 is different from the cross section of the retention portion 21' of the brush head 20', such that when the retention portion 21' of the brush head 20' is retained at the opening 121' of the solution container 10', the clearance 201' is formed between the inner wall of the opening 121' of the solution container 10' and the outer side of the retention portion 21' of the brush head 20'.

The solution container 10' is preferably made of plastic such that a user is able to squeeze the solution container 10' to compress the solution chamber 11 to dispense the solution therein through the opening 121' of the nozzle head 12'. The nozzle head 12' is made to have a supportive and rigid structure to substantially support the brush head 20' so as to prevent the nozzle head 12' from being bent. Accordingly, the nozzle head 12' is integrally extended from the solution container 10' to communicate with the solution chamber 11'. The solution container 10' is embodied as a one-piece integral member adapted to be made by injection molding techniques, so as to minimize the manufacturing cost of the interproximal squirt brush of the present invention.

It is worth mentioning that the solution containers 10, 10' and the brush heads 20, 20' according to the preferred embodiment and their alternatives are interchangeable such that the user is able to select different types of brush head 20 to be used. The solution can be water or medicament commonly sold in market for removing oral bacteria and bad breath. It is worth to mention that the user is able to detach the nozzle head 12 to refill the solution in the solution container. In addition, the solution can be gas solution or liquid solution contained in the solution container 10, 10'.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An interproximal squirt brush, comprising:
a solution container having a solution chamber for containing a solution and a hollow nozzle head having an opening communicating with said solution chamber, wherein a resilient channel is aligned with said opening; and
a brush head having an elongated retention portion replaceably coupling at said opening of said nozzle head and a brush portion extended from said retention portion, wherein a clearance is formed between said opening and said retention portion of said brush head for enabling said solution from said solution chamber being discharged to said brush portion of said brush head along said retention portion, wherein when said retention portion of said brush head is disposed along said resilient channel, an inner wall of said resilient channel is slightly deformed to define said clearance therebetween, wherein said solution container comprises an elastic latch provided at said nozzle head for detachably locking said retention portion of said brush head in position, wherein said resilient channel is defined at said elastic latch to align with said opening, wherein said elastic latch further has a resilient cavity and a latch cavity, wherein said elastic latch comprises a holding member defining said resilient channel therealong, and a locking member having one flexible edge integrally extending from said holding member and an opposed locking edge detachably coupling with said locking member to retain said retention portion of said brush head along said resilient channel, wherein said resilient cavity is provided at said holding member close to said flexible edge of said locking member, wherein said latch cavity is provided at a sidewall of said holding member and arranged in such a manner that when said locking member is folded on said holding member to engage said locking edge with said latch cavity, said resilient cavity is slightly deformed to apply an resilient force at said locking edge of said locking member so as to substantially lock up said locking member with said holding member.

2. The interproximal squirt brush, as recited in claim 1, wherein said resilient channel is positioned between said resilient cavity and said latch cavity, such that when said locking member is folded to said holding member, two sidewalls of said resilient channel are pressed towards each other to slightly deform a size of said resilient channel so as to retain said retention portion of the said brush head in position.

3. The interproximal squirt brush, as recited in claim 2, wherein said locking member further comprises a reinforcing member integrally extended to fit into said resilient cavity for ensuring said resilient force being transmitted to said locking edge of said locking member.

4. The interproximal squirt brush, as recited in claim 3, wherein said reinforcing member has a tapered shape fitting into said resilient cavity.

5. The interproximal squirt brush, as recited in claim 1, wherein said elastic latch is integrally formed with said nozzle head at said opening thereof at a position that said locking member forms at a top surrounding wall of said nozzle head.

6. The interproximal squirt brush, as recited in claim 1, wherein said resilient channel has a non-circular cross section and said retention portion of said brush head has a circular cross section, such that said clearance is formed when said retention portion of said brush head is disposed along said resilient channel.

7. The interproximal squirt brush, as recited in claim 1, wherein said brush head comprises an elongated brush arm defining said retention portion thereat, and a brush member provided at a free end of said brush arm to define said brush portion thereat.

8. The interproximal squirt brush, as recited in claim 7, wherein said brush member comprises a plurality of wire bristles radially extended from said brush arm, such that when said solution is discharged from said opening of said nozzle head, said solution is guided to flow along said brush arm towards said wire bristles of said brush member.

9. The interproximal squirt brush, as recited in claim 7, wherein said brush member comprises a swab element provided at said brush arm, such that when said solution is discharged from said opening of said nozzle head, said solution is guided to flow along said brush arm towards said swab element of said brush member.

10. The interproximal squirt brush, as recited in claim 1, wherein said solution container comprises a solution supplier defining said solution chamber therein and an elongated solution delivering tube extended from said solution supplier to said nozzle head, such that when said solution supplier is actuated, said solution is discharged to said brush head through said clearance.

11. The interproximal squirt brush, as recited in claim 1, wherein said solution container is made of squeezable material arranged in such a manner that when said solution container is squeezed, said solution therein is discharged along said retention portion of said brush head to said brush portion thereof through said clearance.

* * * * *